(12) United States Patent
Yuen

(10) Patent No.: US 7,364,605 B2
(45) Date of Patent: *Apr. 29, 2008

(54) PHOTO-ELECTRONIC AIR PURIFYING DISINFECTOR

(75) Inventor: John Se-Kit Yuen, Kowloon (HK)

(73) Assignee: John Manufacturing Limited, Kowloon (HK)

( * ) Notice: Subject to any disclaimer, the term of this patent is extended or adjusted under 35 U.S.C. 154(b) by 151 days.

This patent is subject to a terminal disclaimer.

(21) Appl. No.: 11/180,593

(22) Filed: Jul. 14, 2005

(65) Prior Publication Data

US 2006/0018805 A1     Jan. 26, 2006

(30) Foreign Application Priority Data

Jul. 19, 2004   (CN)   ................ 2004 1 0069338

(51) Int. Cl.
*B03C 3/016*   (2006.01)
(52) U.S. Cl. ................. 96/16; 96/63; 96/224; 422/121
(58) Field of Classification Search .......... 422/24, 422/121, 186.04, 186.3; 96/16, 224, 63
See application file for complete search history.

(56) References Cited

U.S. PATENT DOCUMENTS

| | | | | |
|---|---|---|---|---|
| 2,638,644 A | * | 5/1953 | Rauhut | 96/142 |
| 3,750,370 A | * | 8/1973 | Brauss et al. | 96/140 |
| 3,798,879 A | * | 3/1974 | Schmidt-Burbach et al. | 96/16 |
| 4,203,948 A | * | 5/1980 | Brundbjerg | 422/121 |
| 5,240,478 A | * | 8/1993 | Messina | 95/273 |
| 5,505,904 A | * | 4/1996 | Haidinger et al. | 422/24 |
| 5,616,172 A | * | 4/1997 | Tuckerman et al. | 96/16 |
| 5,632,806 A | * | 5/1997 | Galassi | 96/16 |
| 5,681,374 A | * | 10/1997 | Von Glehn | 96/16 |
| 5,942,026 A | * | 8/1999 | Erlichman et al. | 96/58 |
| 5,997,619 A | * | 12/1999 | Knuth et al. | 96/224 |
| 6,149,717 A | * | 11/2000 | Satyapal et al. | 96/16 |
| 6,464,760 B1 | * | 10/2002 | Sham et al. | 96/117.5 |
| 6,497,840 B1 | * | 12/2002 | Palestro et al. | 422/24 |
| 2002/0121196 A1 | * | 9/2002 | Thakur et al. | 96/224 |

FOREIGN PATENT DOCUMENTS

| | | |
|---|---|---|
| DE | 10209994 A | 9/2003 |
| GB | 2301179 A | 11/1996 |
| GB | 2402337 A | 12/2004 |

(Continued)

*Primary Examiner*—Richard L. Chiesa
(74) *Attorney, Agent, or Firm*—Mattingly, Stanger, Malur & Brundidge PC

(57) ABSTRACT

A photo-electronic air purifying disinfector firstly filters out airborne impurities using a washable filter screen. It then utilizes an activated carbon filter to filter out airborne bacteria and germs. The bacteria and germs which are capable of passing through the activated carbon filter are then eliminated by extreme-UV light emitted by extreme-UV light tubes. It also utilizes a negative ion generator to boost the level of anions in the air before being discharged. These two modes operate in the following manner: the first mode involves cathodic high-voltage output that is discharged via a carbonized fibre. The ionized air is then expelled by a fan. The second mode eliminates bacteria, germs and mould from air as it passes extreme-UV light tubes by exposure to extreme-UV light emitted by these extreme-UV light tubes.

9 Claims, 9 Drawing Sheets

FOREIGN PATENT DOCUMENTS

| | | |
|---|---|---|
| GB | 2404319 | 1/2005 |
| GB | 2412727 A | 10/2005 |
| JP | 8-238441 | 9/1996 |
| JP | 10-328575 | 12/1998 |
| JP | 2004-16649 | 1/2004 |
| WO | WO 03/086791 | 10/2003 |

* cited by examiner

PHOTO-ELECTRONIC AIR PURIFYING DISINFECTOR

This invention relates to a type of photo-electronic air purifying disinfector. It also relates to a type of photo-electronic air purifying disinfector that uses either a car battery or a mains supply as its power source.

The aim of this invention is to present a new design for this type of photo-electronic air purifying disinfector.

According to an aspect of the present invention, there is provided a photo-electronic air purifying disinfector comprising a housing containing a turbine extractor, an electric motor, one or more extreme-UV light tubes, an air arresting unit, a power supply cable, a cathodic high-voltage carbonized fiber and an activatet carbon filter.

In a preferred embodiment of the disinfector, the air arresting unit concentrates or deflects the airflow into slot(s) containing the extreme-UV light tube(s). This brings the air into close proximity to the extreme-UV light tube(s) for treatment.

The disinfector may firstly filter out airborne impurities using a washable filter screen. It then utilizes the activated carbon filter to filter out airborne bacteria and germs. Bacteria and germs which are capable of passing through the activated carbon filter are then eliminated by extreme-UV light emitted by the extreme-UV light tubes. This invention is capable of eliminating the bacteria, germs and mould contained in air as it passes the extreme-UV light tubes. It also utilize a negative ion generator to boost the level of anions in the air before being discharged.

The main components of a preferred embodiment of this photo-electronic air purifying disinfector include: a washable filter screen, an activated carbon filter, a turbine extractor, extreme-UV light tubes, an electric motor and a cathodic high-voltage fibre. When air enters the photo-electronic air purifying disinfector via the turbine extractor, the impurities in the air are filtered out via a washable filter screen. Airborne bacteria and germs are then filters out via an activated carbon filter. The device has first and second continuous alternating mode cycles: the first involves high voltage cathodic output discharged via a carbonized fibre which ionizes the air which is then expelled by the fan; the second involves turning on extreme-UV light tubes which emit extreme-UV light eliminating airborne bacteria, germs and mould as they pass the tubes. This photo-electronic air purifying disinfector possesses an air inlet and an air outlet. The cathodic high-voltage carbonized fibre is located at the air outlet. The extreme-UV light tubes are located within the housing close to the air outlet. The turbine extractor, located within the housing close to the air inlet, sucks air through the air inlet grille unit into the housing. The air then streams through the activated carbon filter prior to exposure to and serialization of germs, bacteria and mould by extreme-UV light emitted by the extreme-UV light tube. The air is ionised before being discharged through the air outlet as clean, fresh air, thereby exchancing air quality indoors.

This device is of a square column shade.

A preferred non-limiting embodiment of the parent invention will now be described with reference to the accompanying diagrammatic drawings, in which.

Figure 1:
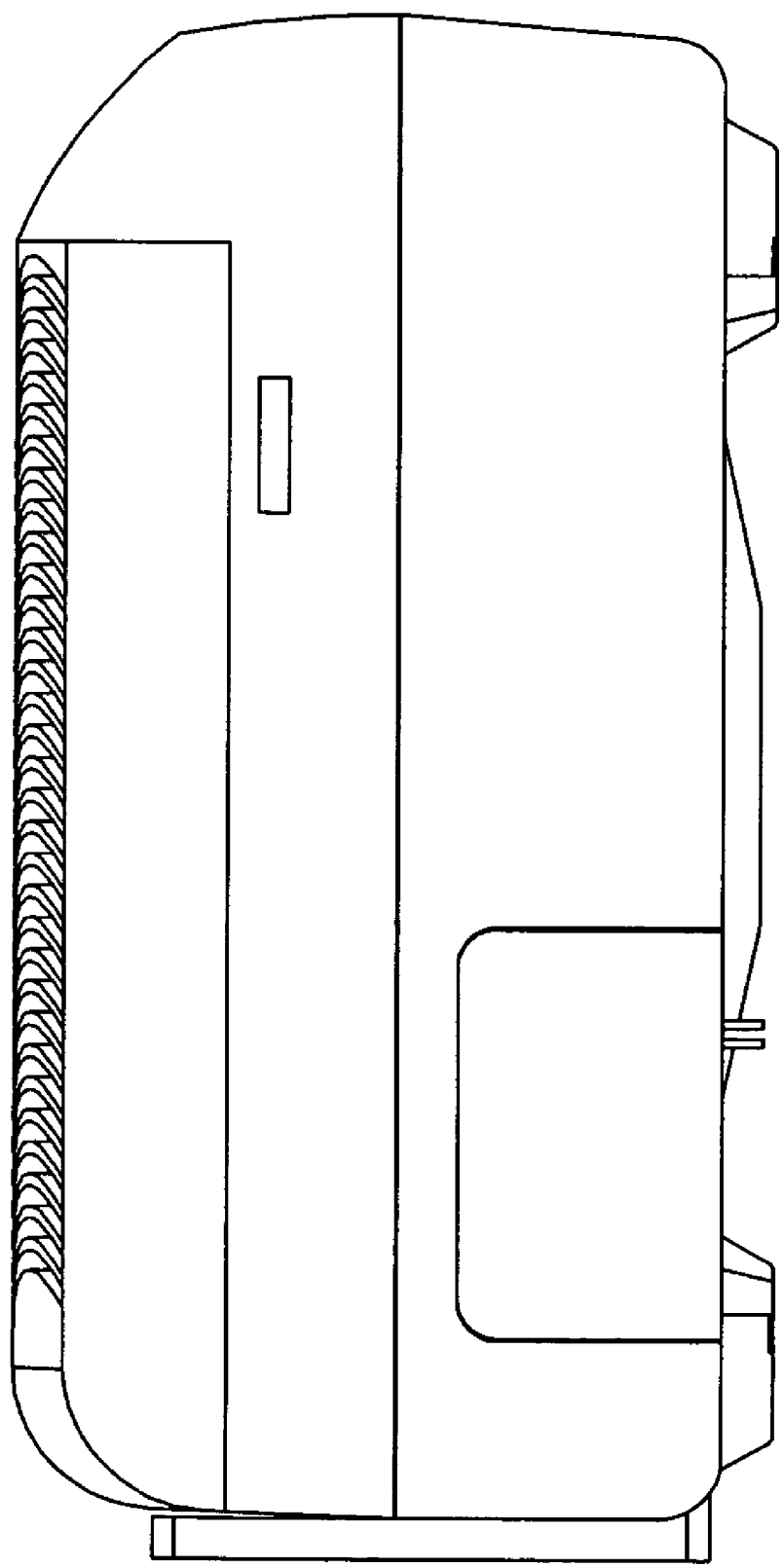
FIG. 1 is a side elevation view of a photo-electronic air purifying disinfector in accordance with a preferred embodiment of the present invention.

The photo-electronic air purifying disinfector consists of a square-column-shaped housing 1, with a rectangular air outlet grille 2 located on top of the rear housing 3. Located close beneath the air outlet grille 2 is a filter frame 5. On the front of the housing 1 there is an external grille 4. After ionization, air is expelled via the air outlet grille 2.

Figure 2:
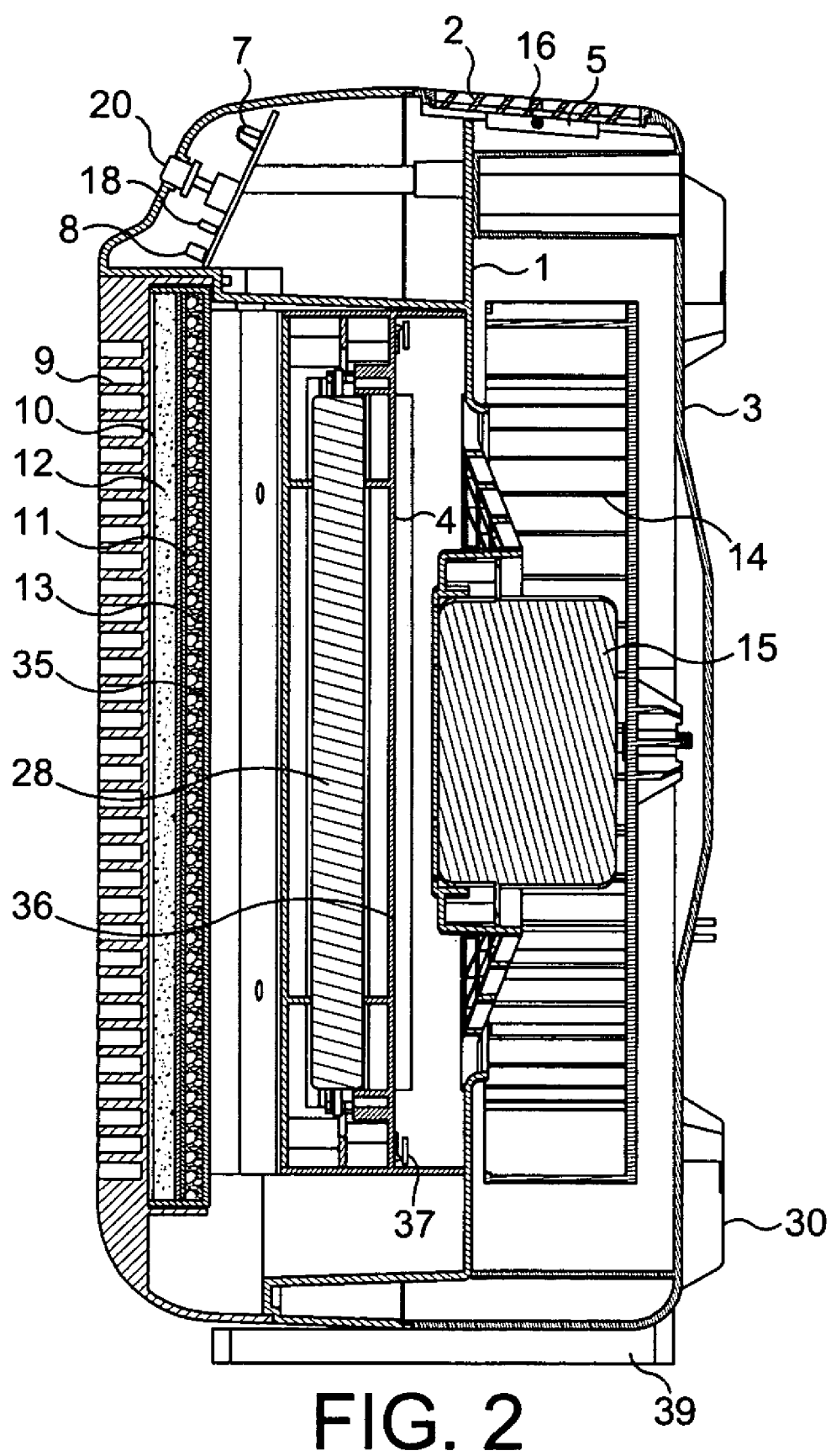
FIG. 2 is a longitudinal cutaway view of the product depicted in FIG. 1.
Figure 3:
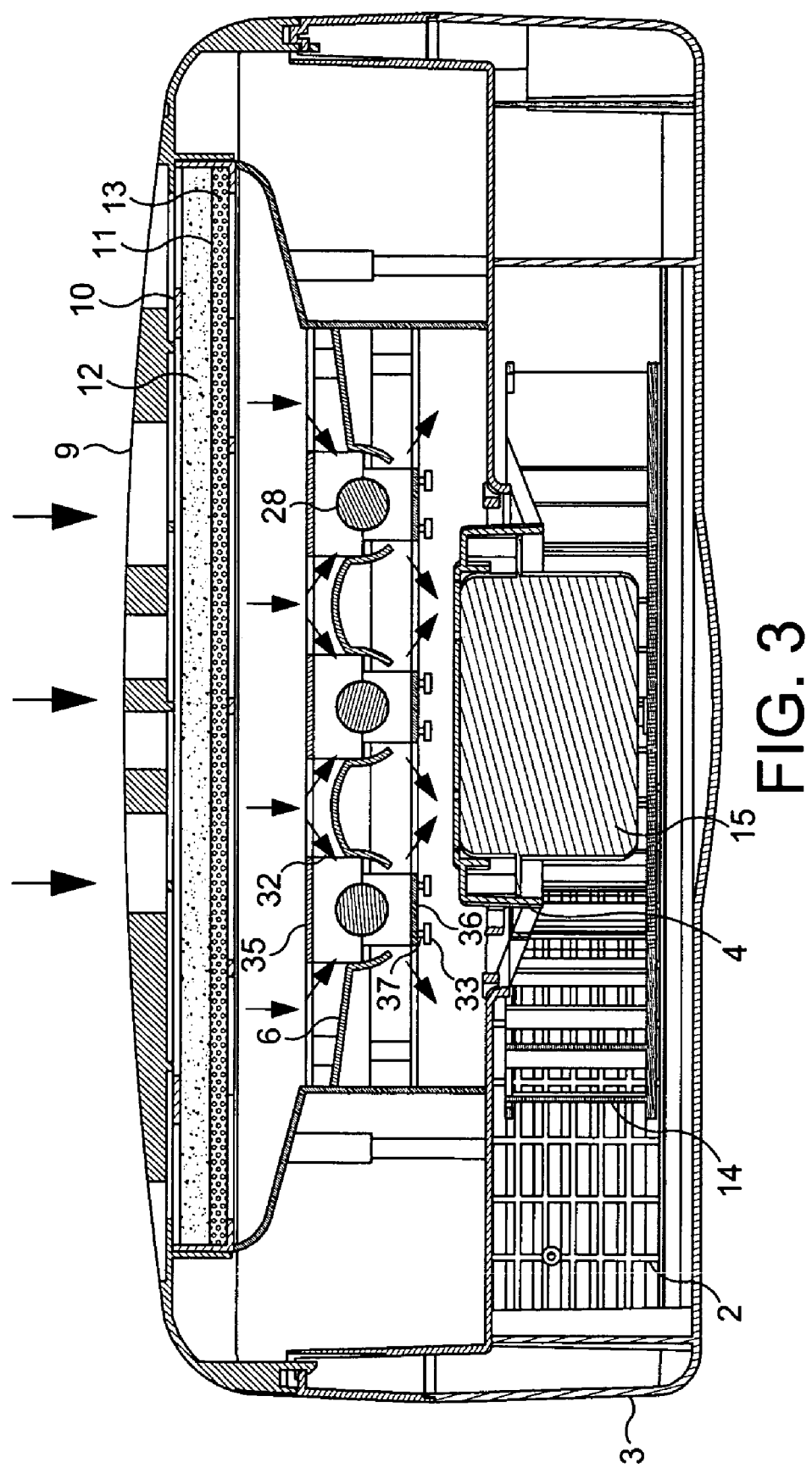
FIG. 3 is a horizontal cutaway view of the product depicted in FIG. 1.
Figure 4:
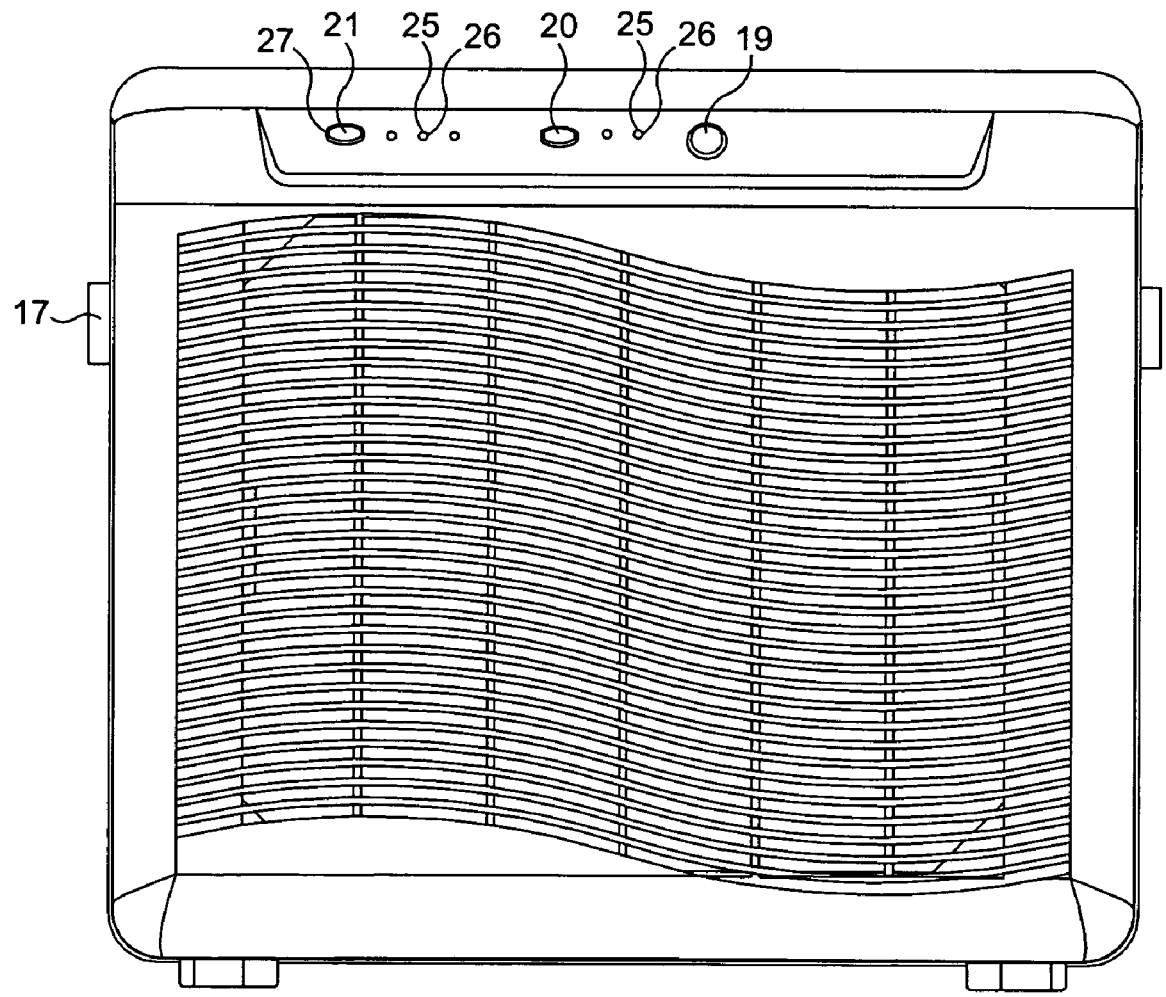
FIG. 4 is a plan view of the product depicted in FIG. 1.
Figure 5:
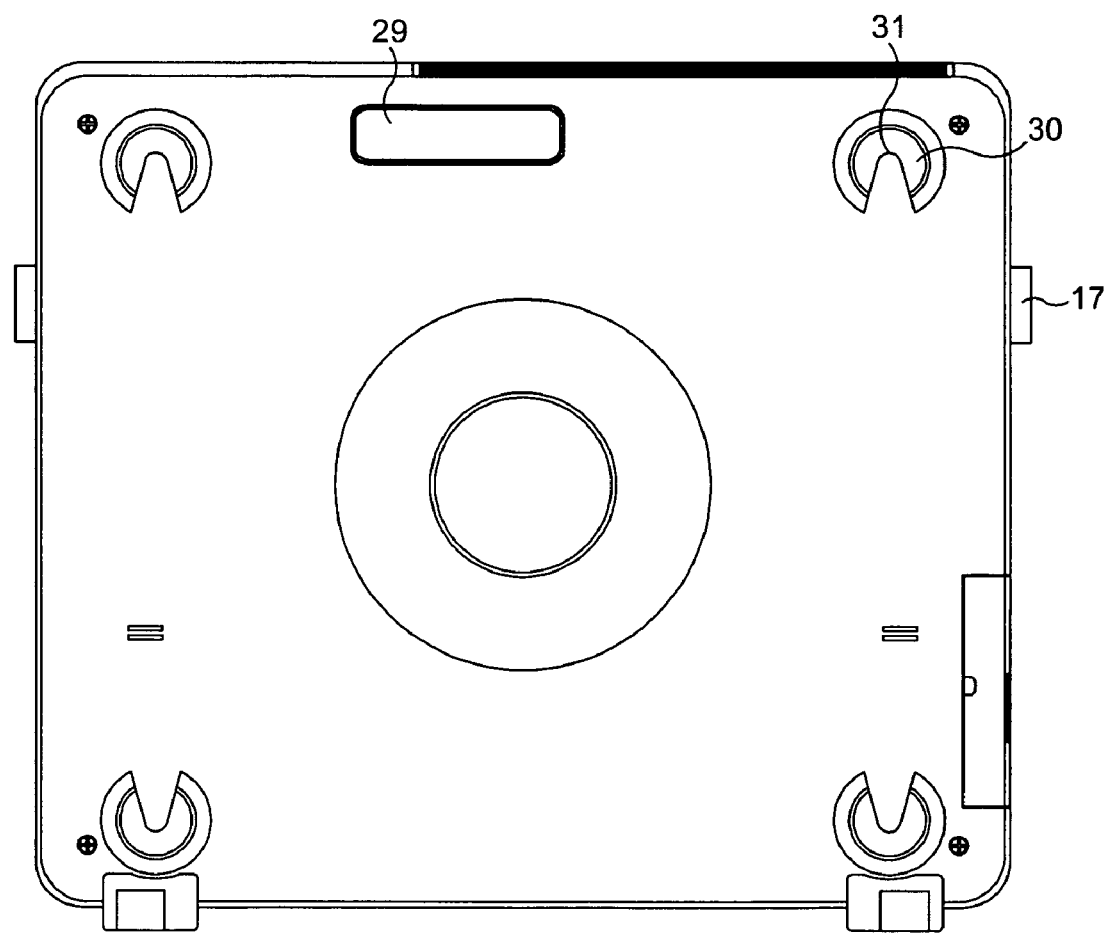
FIG. 5 is an end-view of the product depicted in FIG. 1.
Figure 6:
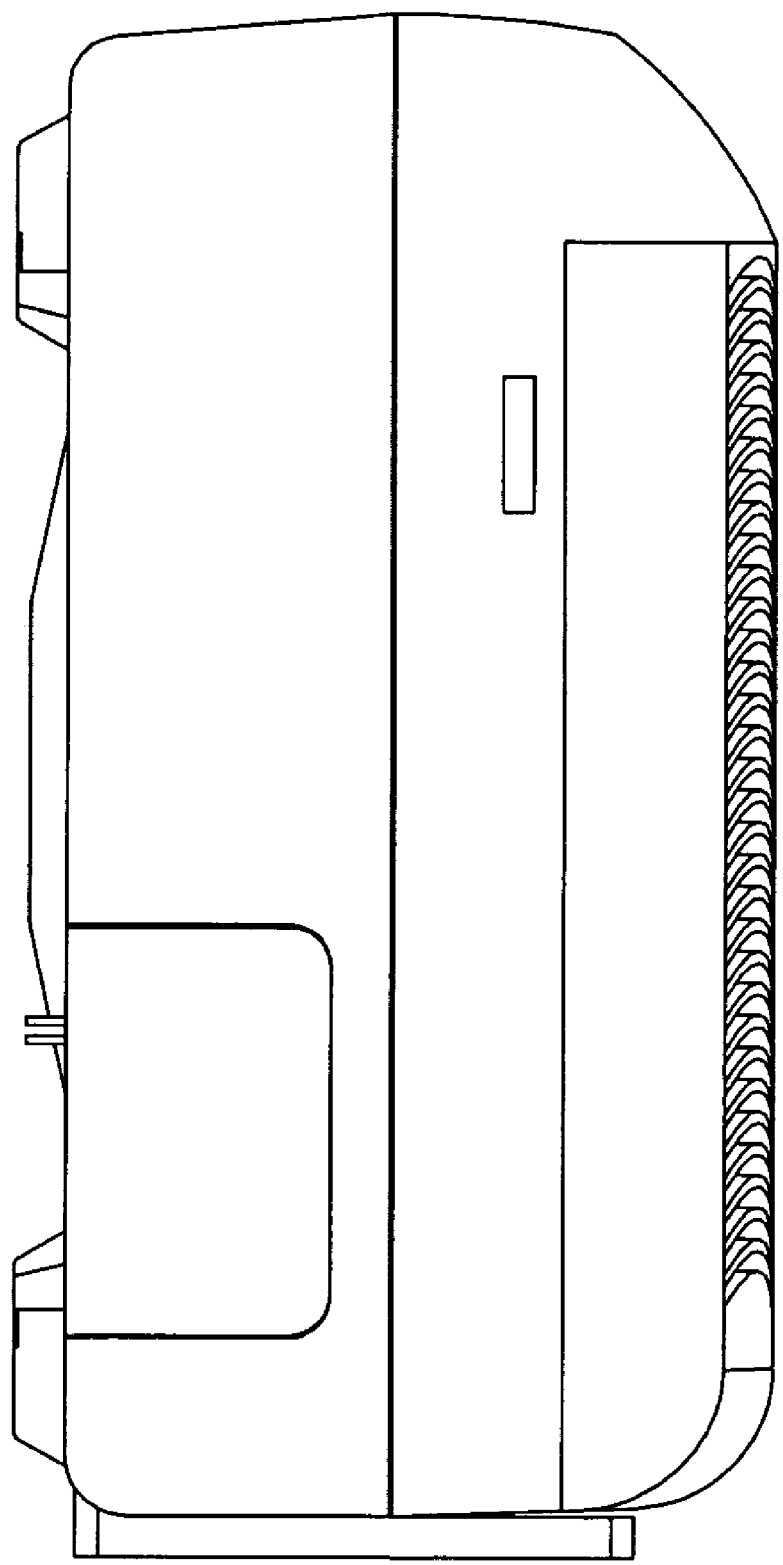
FIG. 6 is a side elevation view of the other side of the product depicted in FIG. 1.
Figure 7:
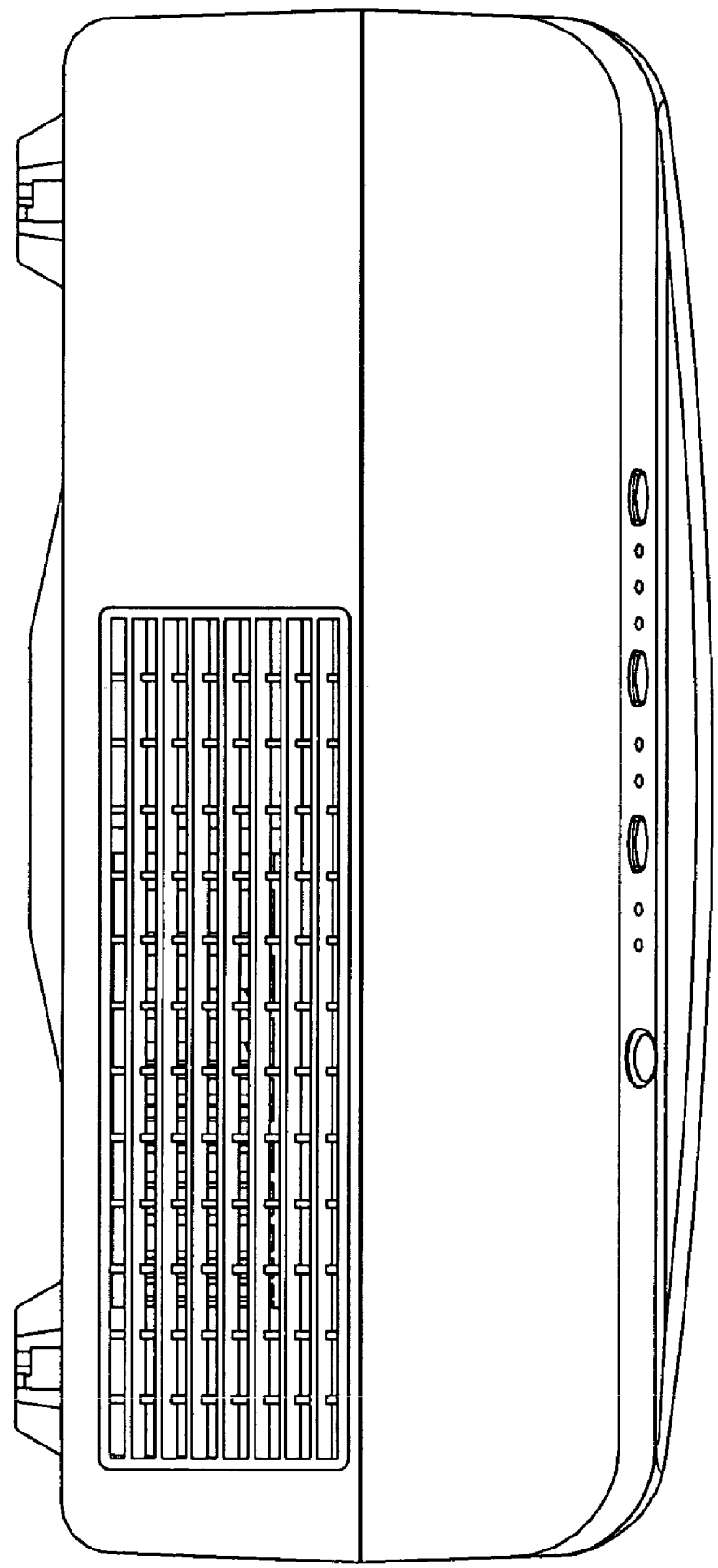
FIG. 7 is an upward view of the product depicted in FIG. 1.
Figure 8:
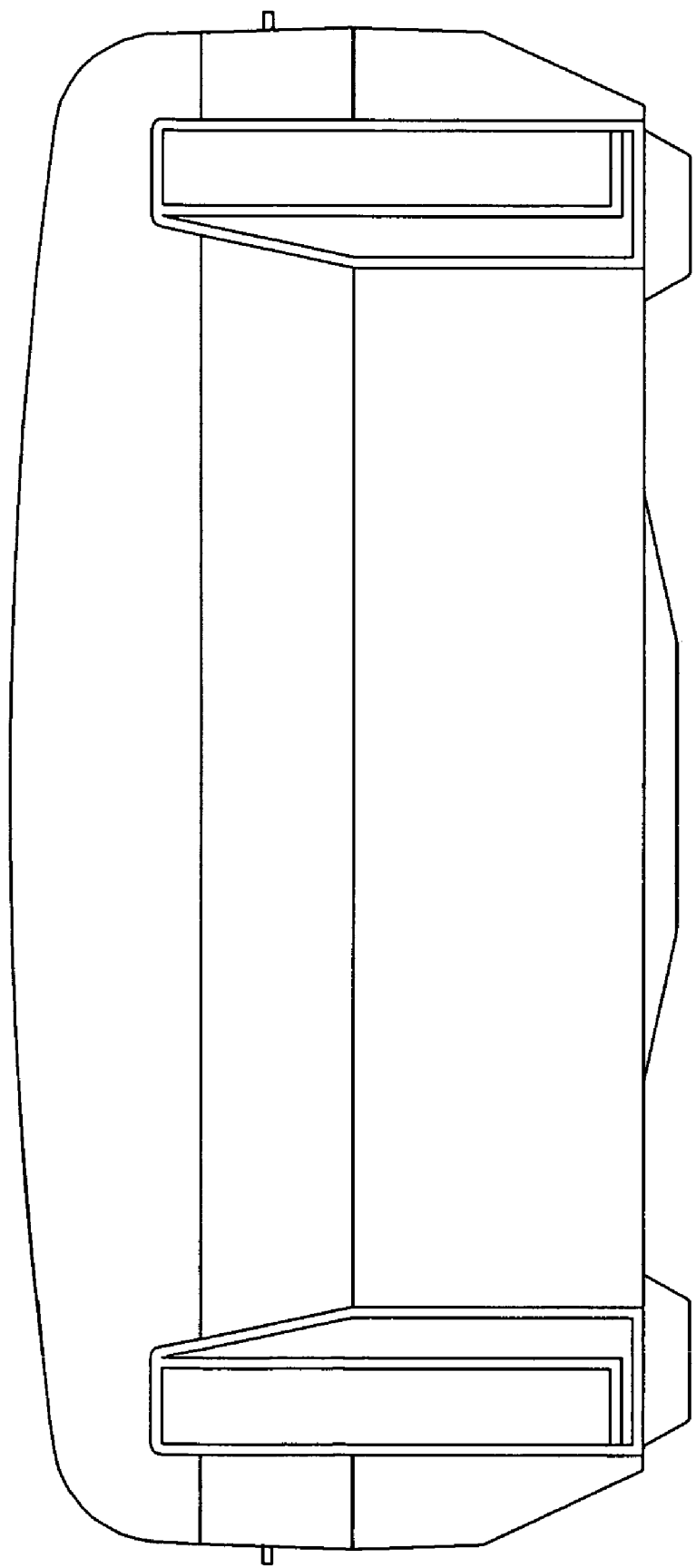
FIG. 8 is a downward view of the product depicted in FIG. 1.
Figure 9:
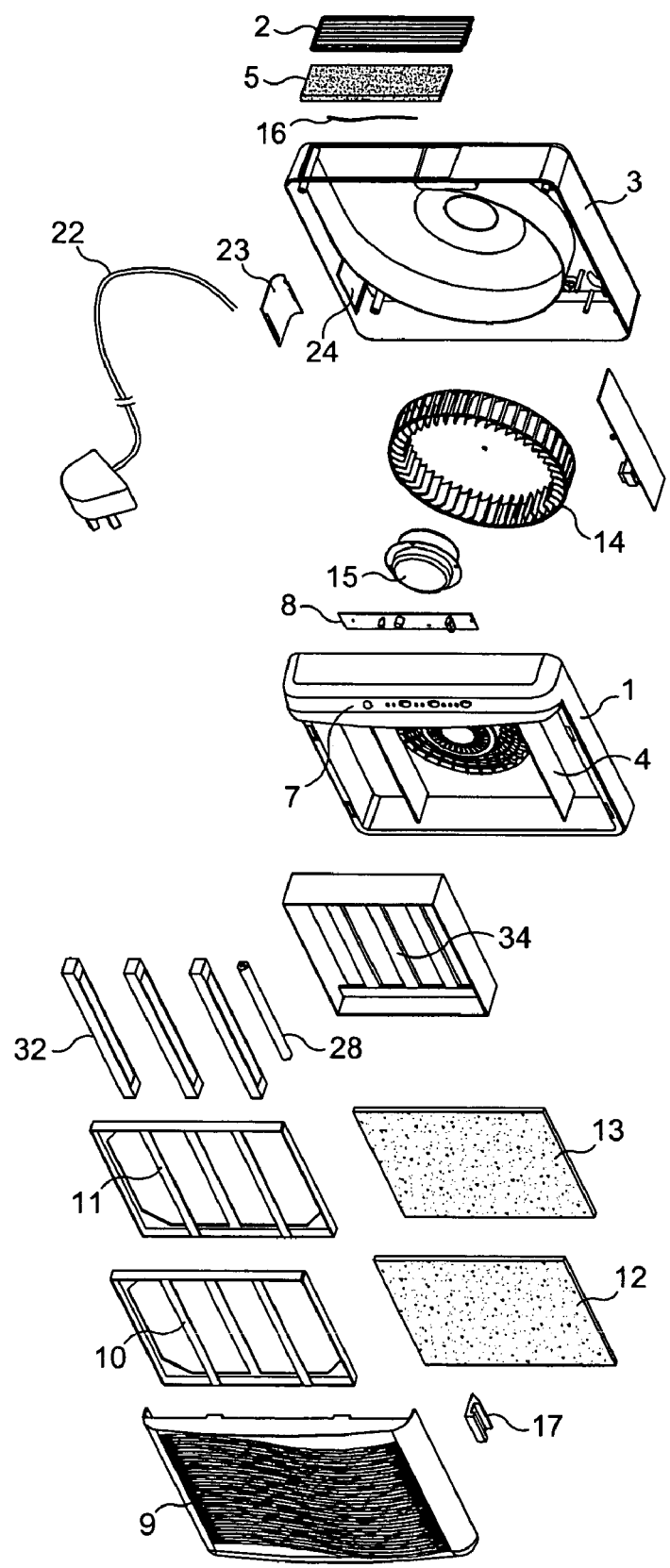
FIG. 9 is an exploded schematic diagram of the product depicted in FIG. 1.

The detailed structure of the photo-electronic air purifying disinfector is shown in FIG. 2. There is an air inlet grille 4 on the top of the front of the housing 1. This air inlet grille 4 provides an air intake. There is an air arresting unit 6 connected to the front end of the air inlet grille 4. On the top end of the housing 1 there is a control panel cover 7, which secures the electrical function circuit equipment 8. There is a protective cover 9 on top of the front of the housing 1, which secures the washable filter screen frame 10 and the activated carbon filter frame 11. The washable filter screen frame 10 is fitted with a foam rubber dust filter 12. The activated carbon filter frame 11 is fitted with an activated carbon filter 13. Close to the internal surface of the air inlet grille 4 is the turbine extractor 14 and the electric motor 15. The cathodic high-voltage carbonized fibre 16, fixed at the centre of the front surface of the air outlet grille 2, performs an air ionizing function. On the left and right end of the top of the protective cover 9 there are separate catches 17. By pressing them down, users are able to lift up the protective cover 9 in order to clean the foam rubber dust filter 12 or to replace the activated carbon filter 13.

There is an electronic generator 18, a function indicator light 19, a function selector switch 20 and a timer 21 located within the control panel cover 7 on the top of the housing 1. There is a power cable cover 23 and a power cable recess 24 located within the bottom of the side of the housing 1, which allows the power cable 22 to be retracted. There are a number of circular holes 25 located on the front surface of the control panel cover 7, which contain light-emitting diodes 26 of different colours, which act as function indicators. There are three elongated holes 27, which contain the function indicator light 19, the function selector switch 20 and the timer 21. The function selector switch 20 controls the functioning of the electric motor 15, the turbine extractor 14, the extreme-UV light tubes 28 and the carbonized fibre 16.

There is a hand hold 29 on the back of the rear housing 3 and four supports 30. The hand hold 29 allows users to pick up the photo-electronic air purifying disinfector easily. The four supports 30 contain screw holes 31 which allow users to hang the photo-electronic air purifying disinfector on a wall for use. There are two flat surface feet 39 on the bottom of the rear housing 3, which allow the photo-electronic air purifying disinfector to stand on any flat surface.

There is an air arresting unit 6 connected to the air inlet grille 4 on the top of the front of the housing 1. The air arresting unit 6 includes three extreme-UV light tube module recesses 32. These extreme-UV light tube module recesses 32 possess four metallic contacts 33. These four metallic contacts 33 conduct electricity and are in contact with the air arresting unit's main structure 34. The main structure 34 is made up of the large front light shield 35, the rear small light shield 36, the extreme-UV light tubes 28 and the metallic contacts 37. On the left and right end of the top of the protective cover 9 on the front of the housing 1 there are separate catches 17. By pressing them down, users are able to lift the protective cover 9 open in order to remove and clean the air arresting unit 6 or replace the extreme-UV light tubes 28.

When the photo-electronic air purifying disinfector is switched on, air containing bacteria, germs and mould is sucked by the turbine extractor 14 into the extreme-UV light tube module recesses 32 through the protective cover 9, the rubber foam dust filter 12 and the activated carbon filter 13. Air streams through the air-arresting units 37 in the extreme-UV light tube module recesses 32 before reaching the air outlet grille 2. The extreme-UV light tubes 28 are mounted in the centre of the air-arresting units 37, where air is disinfected by the extreme-UV light on reaching the air portals 38. The purified air is then drawn through the air outlet grille 2 where it is ionised by the cathodic high-voltage carbonized fibre 16 prior to eventual discharge from the air outlet grille 2.

There is a large light shield 35 located at the front of the air arresting unit's main structure 34, and small light shield 36 located at its rear. These prevent extreme-UV light emission from escaping from the housing 1, thus protecting the eyes of users.

The principles of the electrical circuits of the photo-electronic air purifying disinfector are: the power supply input reaches the anion-producing circuitry via the function selector switch 20, providing a negative high-voltage output. The power supply input also passes through a full wave rectifier circuit to supply power to a speed control circuit, which supplies the turbine extractor 14, then passes through a DC to AC conversion circuit, to run the full wave rectifier extreme-UV light tubes 28 circuit; another circuit passes a DC voltage stabilizing circuit to reach the ioniser circuit and supplies power to the automatic cycle control circuit of the extreme-UV light tubes 28 activation circuit, controlling the alternating operation of the ioniser and the extreme-UV light tubes 28.

The extreme-UV light tubes emit ultraviolet light at the wavelength of 253.7 nanometers, which has been proven scientifically to be most effective in eliminating bacteria, germs and mould in the air. An increased level of anions in the air caused by the anion generator helps boost the biochemical reactions in our body and reduces hormonal secretions held responsible for depression and tiredness. The invention therefore serves well in most households, hospitals, residential homes, department stores, cinemas, restaurants, offices, workshops, vehicles, ships, airplanes and trains. This 3-in-1 photo-electronic air purifying disinfector will improve the environments in our homes, hospitals, offices, shops and transportation. It also helps to revitalise air quality amidst the constant degradation of our natural environment.

The invention claimed is:

1. A photo-electronic air purifying disinfector comprising a housing containing a turbine extractor, an electronic motor for driving the turbine extractor to produce an airflow, one or more extreme-UV light tubes, one or more air arresting units, a power supply cable, a cathodic high-voltage carbonized fibre and an activated carbon filter, wherein the one or more air arresting units concentrates or deflects the airflow into a slot containing a respective one of the one or more extreme-UV light tubes.

2. The disinfector according to claim 1, wherein the housing has a generally square-column shape.

3. The disinfector according to claim 1, wherein the housing also contains an electrical circuit board, switches and indicator lights for controlling the operation of the disinfector.

4. The disinfector according to claim 1, wherein the air arresting unit has a front and a back light shield, which prevent extreme-UV light from escaping from the housing, thus protecting the user's eyes.

5. The disinfector according to claim 1, wherein the one or more extreme-UV light tubes are removable and may be replaced.

6. The disinfector according to claim 1, wherein the filter is removable and may be replaced.

7. The disinfector according to claim 1, wherein the housing has a hand hold which allows easy manhandling, and in addition the disinfector may be hung on a wall.

8. An electrical circuit system that is capable of improving specific characteristics of the environment, specifically for use in purifying indoor air and increasing the level of anions contained in the air, wherein the electrical circuit system includes:
   a negative ion generating circuit for a cathodic high-voltage carbonized fibre; and
   a circuit which enables the emission of UV light at the wavelength of 253.7 nm from one or more extreme-UV light tubes;
   wherein the electrical circuit system has first and second modes, the first mode involving cathodic high-voltage output discharged via the cathodic high-voltage carbonized fibre, the ionized air containing the anions then being expelled by a turbine extractor; the second mode involving turning on the one or more extreme-UV light tubes which emit extreme-UV light eliminating airborne bacteria, germs and mould as they pass the tubes, and the electrical circuit system in addition allows a user to choose to operate in the first mode or in the second mode separately, to choose continuous simultaneous operation or to choose operation of the two modes in a continuous alternating cycle.

9. The electrical system according to claim 8, wherein a value of the cathodic high-voltage output is within the range of 4.5 kV to 8.5 kV.

* * * * *